United States Patent

Woods et al.

[11] 4,058,752
[45] Nov. 15, 1977

[54] DOSIMETRY CONTROL METHOD

[75] Inventors: William C. Woods, Lynn; Robert E. Levin, South Hamilton; Richard H. Hodges, Marblehead, all of Mass.

[73] Assignee: GTE Sylvania Incorporated, Danvers, Mass.

[21] Appl. No.: 721,918

[22] Filed: Sept. 9, 1976

[51] Int. Cl.² .................. H05B 41/36; H05B 37/02
[52] U.S. Cl. ............................... 315/360; 250/504; 315/107; 315/128; 355/69
[58] Field of Search ............ 315/360, 119, 128, 293, 315/106, 107; 250/354, 355, 504; 355/35, 69

[56] References Cited

U.S. PATENT DOCUMENTS 3,344,704  10/1967  Simpson et al. .................. 355/69
3,738,242   6/1973  Lee et al. ......................... 355/69 X
3,909,659   9/1975  Van Der Meulen ............ 315/360 X

FOREIGN PATENT DOCUMENTS 2,352,500   4/1975  Germany ........................ 250/504

Primary Examiner—Eugene R. LaRoche
Attorney, Agent, or Firm—James Theodosopoulos

[57] ABSTRACT

In a method of operating a photochemotherapy chamber for the irradiation of a patient with long wave ultraviolet light, a prescribed dosage is first selected. The prescribed dosage is then automatically converted into the time duration that an ultraviolet source should be energized to deliver said dosage by monitoring the line voltage and the total hours of operation of the ultraviolet source and adjusting said time duration accordingly.

1 Claim, 2 Drawing Figures

DOSIMETRY CONTROL METHOD

THE INVENTION

The purpose of this invention is to provide a method of automatically controlling the exposure dosage of ultraviolet radiation that a patient receives. This method may be used with the ultraviolet irradiation chamber disclosed in copending application Ser. No. 693,029, filed June 4, 1976. The objectives of the invention are to provide a control system that will automatically compensate for the normal decrease in output of ultraviolet lamps during life and to provide a timing device the output of which will vary the basic time increment in accordance with a linear or nonlinear equation or curve.

The invention is based on the relationship that the irradiation dosage (joules/cm$^2$) equals the irradiance (watts/cm$^2$) at the time of exposure multiplied by the exposure time (seconds).

Figure 1:
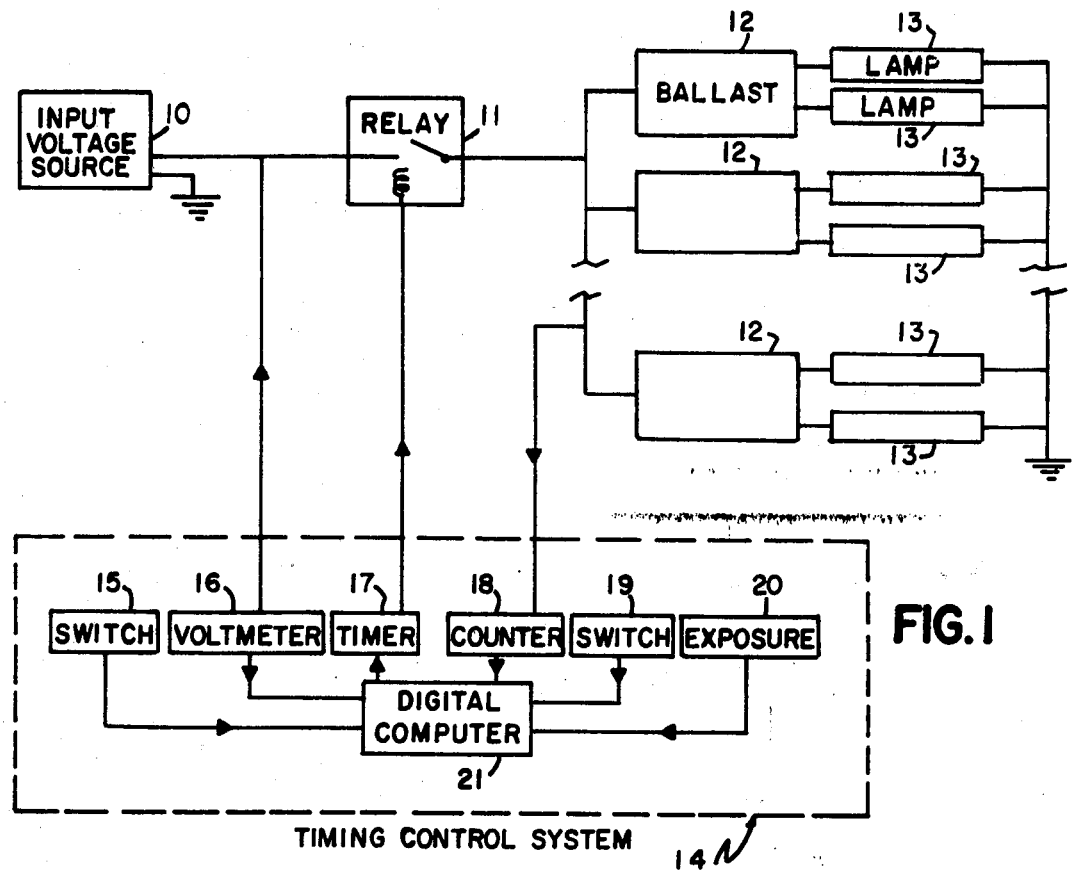
FIG. 1 is a schematic block diagram of a dosimetry control unit that can be used to practice the invention.

In operation, power from an input voltage source 10 is delivered through a relay 11 to ballasts 12 and ultraviolet emitting lamps 13. The lamps are energized and radiate only when relay 11 is energized. Relay 11 is energized by a timing control system 14.

Timing control system 14 is made up of several functional elements. The dose of ultraviolet radiation is defined to the system by a manually adjustable multiposition switch 15 which modifies a digital signal within a digital computer 21. The dose is set in joules per square centimeter. The voltage to the lamps is monitored by an analog to digital device 16, such as a digital voltmeter, which supplies a digital signal to computer 21. A cumulative counter 18 is also energized by the voltage to the ballasts and produces a digital signal which is proportional to the cumulative hours which the lamps have operated since they were installed. The digital signal from counter 18 is supplied to digital computer 21. Counter 18 is manually reset to zero each time a new set of ultraviolet lamps is installed in the system.

Manually closing a contact in an initiate switch 19 starts computation of the exposure time by computer 21 according to the mathematical relations described hereafter. The computer then sets timer 17 to the required exposure time which energizes relay 11, thereby energizing lamps 13. Upon completion of the calculated exposure time, timer 17 de-energizes relay 11 thus deactivating lamps 13. Consequently, lamps 13 are on only for the time required to deliver the prescribed dose of ultraviolet radiation.

Digital computer 21 stores three pieces of information. It stores the relationship of the output of ultraviolet lamps 13 to the voltage of input voltage source 10. This relationship depends on both ballast 12 and lamp 13 characteristics. The relationship is nonlinear and the output decreases with voltage. For example, in a system designed for 120 volts, if the input voltage drops to 100 volts, the lamp output drops about 12%.

Figure 2:
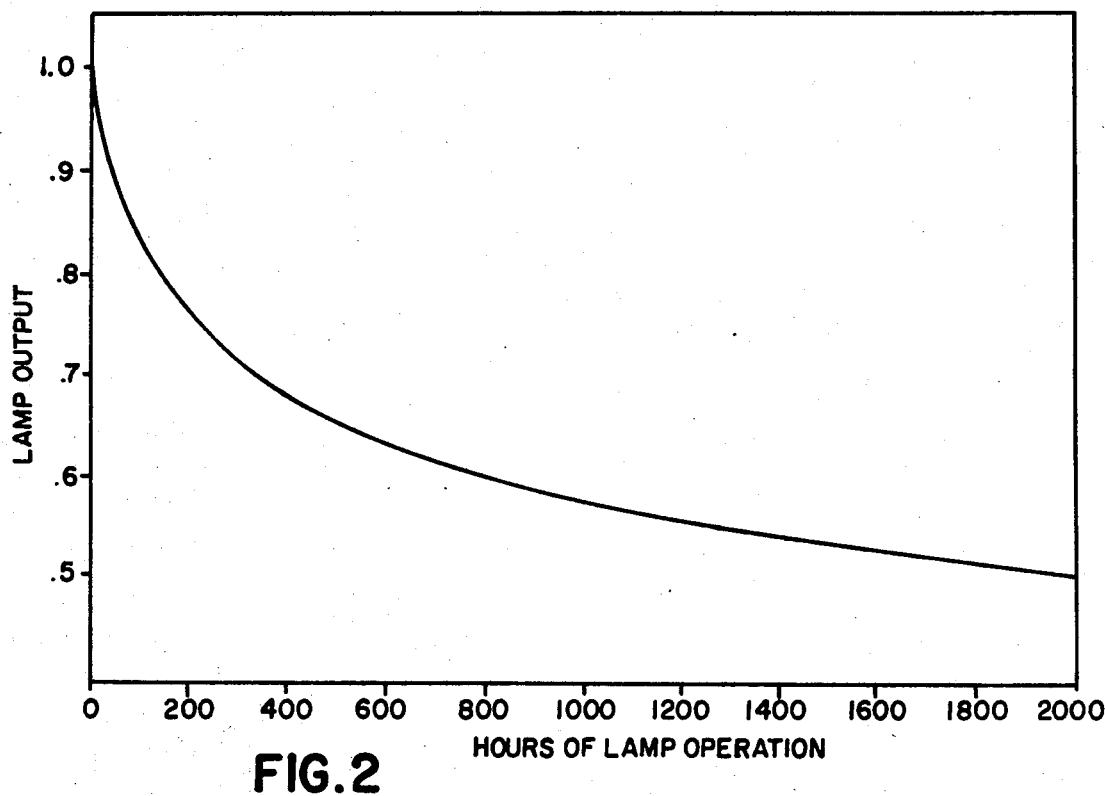
FIG. 2 is a curve showing the decrease in output of ultraviolet lamps versus their cumulative hours of operation.

Computer 21 also stores the fractional decrease in ultraviolet lamp output as a function of cumulative hours of lamp operation. This characteristic is a function of the lamp and especially of the phosphor. FIG. 2 shows the nonlinear decrease in lamp output versus cumulative hours of operation.

Computer 21 also stores the exposure power density provided on a patient in the chamber with new lamps and rated equipment input voltage. While this is a constant function, the value may be internally modified by exposure calibrator 20 for the purpose of calibrating the entire dose control system. In one example for a chamber containing sixty FR40T12/BL/235° fluorescent lamps, the exposure power density is 15 milliwatts per square centimeter.

In operation a doctor would prescribe a particular dosage of ultraviolet radiation, say, ten joules per square centimeter. Multiposition switch 15 would then be set at ten. Closing initiate switch 19 would activate the system and, for new lamps and rated line voltage, computer 21 would calculate the exposure time for the above chamber to be 667 seconds (1 joule equals 1 watt-second); timer 17 would energize lamps 13 for that period of time. If the lamps had been in use for 200 hours, as recorded by counter 18, FIG. 2 shows that the lamp output would be only 75% of its zero hour output. Computer 21 would incorporate this calculation and set the exposure time at 888 seconds.

We claim:

1. The method of operating a photochemotherapy chamber for the irradiation of a patient with long wave ultraviolet light comprising the steps of:
   1. selecting a prescribed dosage of long wave ultraviolet radiation;
   2. automatically converting said prescribed dosage into the time duration that an ultraviolet source should be energized to deliver said dosage by
      a. monitoring the line voltage delivered to said ultraviolet source and establishing said time duration in accordance with the deviation of said line voltage from a predetermined value and
      b. monitoring the hours of operation of said ultraviolet source and establishing said time duration in accordance with a nonlinear curve of output versus hours of operation for said ultraviolet source; and
   3. exposing the patient to said ultraviolet radiation for said time duration.

* * * * *